United States Patent [19]

Uchida et al.

[11] Patent Number: 4,672,970

[45] Date of Patent: Jun. 16, 1987

[54] ELECTRODE FOR LIVING BODY

[75] Inventors: Teruyoshi Uchida; Hisayoshi Yamamori, both of Nagoya; Hirotaka Kojima, Kasugai; Junichi Tashita, Nagoya, all of Japan

[73] Assignee: Mitsubishi Rayon Company, Ltd., Tokyo, Japan

[21] Appl. No.: 760,115

[22] Filed: Jul. 29, 1985

Related U.S. Application Data

[63] Continuation-in-part of Ser. No. 635,528, Jul. 30, 1984.

[30] Foreign Application Priority Data

Jan. 31, 1985 [JP] Japan .................................. 60-17528
Mar. 12, 1985 [JP] Japan .................................. 60-49139

[51] Int. Cl.$^4$ .............................................. A61B 5/00
[52] U.S. Cl. ................................. 128/635; 204/403; 204/415; 204/431
[58] Field of Search ................ 128/635; 204/403, 415, 204/431, 433

[56] References Cited

U.S. PATENT DOCUMENTS 3,911,901 10/1975 Niedrach et al. .................... 128/635
4,442,841  4/1984 Uehara et al. ....................... 128/635
4,534,355  8/1985 Potter ................................. 128/635

FOREIGN PATENT DOCUMENTS 0169668 10/1982 Japan .................................. 128/635

OTHER PUBLICATIONS

Brown et al., "Oxygen Transport to Tissue", Pharmacology, Math Studies and Neonatology, pp. 1103–1108, 1973.

*Primary Examiner*—Lee S. Cohen
*Attorney, Agent, or Firm*—Oblon, Fisher, Spivak, McClelland & Maier

[57] ABSTRACT

Disclosed is a metal electrode for a living body, which comprises a noble metal wire an an insulating covering layer formed around the periphery of the noble metal wire. At least a part of the portion of the insulating covering layer falling in contact with the noble metal wire is composed of a crosslinked epoxy resin. The outermost layer of the insulating covering layer is composed of a polyurethane. Either or both of a part of the tip end and side face of the metal electrode is directly covered with a polyurethane porous membrane instead of the insulating covering layer. The electrode is advantageous in that (a) the adhesion of a membrane to the insulating covering layer and the adhesion of the insulating covering layer to a metal wire of the electrode are excellent, (b) measurement can be stably performed for a long time, (c) a stablization time required for obtaining a stable current value at the initial stage of the measurement is short, and (d) the electrode can be handled very easily and has enhanced measurement precision and response characteristics.

4 Claims, 1 Drawing Figure

ELECTRODE FOR LIVING BODY

This application is a continuation-in-part of parent application Ser. No. 635,528, filed July 30, 1984.

BACKGROUND OF THE INVENTION (1) Field of the Invention

The present invention relates to an improvement in a metal electrode for continuously measuring changes in the oxygen partial pressure of a living body. More particularly, it relates to an improvement in a metal electrode for measuring the oxygen partial pressure by utilizing the principle of the polarography, in which the measurement precision and stability are increased.

(2) Description of the Related Art

Methods for electrically measuring concentrations of living body components in blood or tissues by using electrodes have long been known. In particular, methods utilizing the principle of polarography have been widely used for measuring concentrations of the oxygen gas component and various ion components, especially for continuously measuring changes in the concentrations of these components. Although various components are measured as living body components in blood or tissues, the following description will be made with reference to the measurement of the oxygen partial pressure as an example. In the measurement method utilizing polarography, an electrode of a noble metal such as gold, platinum or silver and a reference electrode of silver/silver chloride or the like are used, and a micro-voltage is imposed between both electrodes to effect a reduction of oxygen on the surface of the working electrode (cathode). The oxygen concentration in a solution is determined by measuring the reduction current generated.

The oxygen gas concentration (oxygen partial pressure) in a living body has an important influence on that body. For example, it is considered important to know, precisely and continuously, any changes in the oxygen partial pressure in new-born babies or during anesthesia, cardiac surgery, brain surgery, and digestive organ surgery. There is also an increased demand to measure changes in the oxygen partial pressure by inserting the electrode directly into the blood vessel or living body tissue, when such measurement is considered necessary.

An important factor in the above-mentioned measurement method is the diffusion current based on the oxygen concentration gradient between the surface of the cathode and the solution. Movement of the cardiac muscle and pulsation of the blood is constant and continuous in a living body, and the diffusion current is greatly influenced by these motions of the living body. Therefore, it is very difficult to precisely measure a small oxygen partial pressure. ExtensiVe efforts have been made heretofore to eliminate this defect. Namely, there has been proposed a composite electrode, comprising working and reference electrodes and an electrolyte, which are enveloped in an oxygen-permeable membrane (see U.S. Pat. No. 3,957,613). Also, there has been proposed a method in which the surface of a working electrode is covered with a hydrophilic water-swelling membrane of polyhydroxyethyl acrylate, cellophane or the like, so that oxygen is moved to the surface of the electrode through water captured among the polymer molecules (see U.S. Pat. No. 3,912,614). These composite electrode and method have been practically adopted. However, the composite electrode has a large size and, therefore, it can be inserted only into a specific portion, for example, a large blood vessel. In the above-mentioned method, the measurement sensitivity varies depending upon the particular state in which the water-swelling membrane is held and, hence, the measurement precision is low. Furthermore, the membrane becomes brittle and is readily broken on drying. We carried out research into the development of an electrode for a living body which can be inserted into any portion of the tissue and blood vessel of the living body and is also capable of precisely measuring the oxygen partial pressure continuously and stably without being influenced by motion of the tissue or blood vessels. Consequently, in Japanese Unexamined Patent Publication No. 57-117838, we proposed an electrode for a living body, which comprises a metal wire electrode covered with a porous membrane. However, this membrane-covered electrode is suffers from insufficient adhesion between the insulating covering layer and the metal wire and the adhesion of the porous membrane, and thus the measurement cannot be performed stably for a long period. Moreover, when many electrodes are produced under the same conditions, large deviations in the output values are observed in the formed electrodes.

Accordingly, development of an electrode for a living body, in which the foregoing defects are eliminated, has been eagerly desired.

SUMMARY OF THE INVENTION

The present invention has now been completed under the above-mentioned background. It is therefore a primary object of the present invention to provide an electrode for a living body, which is advantageous in that (i) it has an excellent adhesion of a membrane to the insulating covering layer, and adhesion of the insulating covering layer to a metal wire of the metal electrode, (ii) measurement can be stably performed for a long period (iii) a so-called stabilization time required for obtaining a stable current value at the initial stage of the measurement is short, (iv) the electrode can be handled very easily, and (v) the electrode has enhanced measurement precision and response characteristics.

More specifically, in accordance with the present invention, there is provided a metal electrode for a living body, which comprises a noble metal wire and an insulating covering layer formed around the periphery of the noble metal wire, wherein at least a part of the portion of the insulating covering layer falling in contact with the noble metal wire is composed of a crosslinked epoxy resin, the outermost layer of the insulating covering layer is composed of a polyurethane, and either or both of a part of the tip end and side face of the metal electrode is directly covered with a polyurethane porous membrane instead of the insulating covering layer.

DESCRIPTION OF THE PREFERRED EMBODIMENTS

Figure 1:
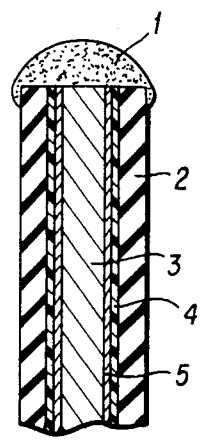
FIG. 1 is an enlarged sectional view showing an example of the tip end portion of the electrode according to the present invention.

The noble metal wire used in the present invention is a metal wire of a noble metal such as gold, silver or a platinum group element, or a mixture thereof. Because the metal wire must invade the living body at the time of insertion of the electrode, it is preferred that the diameter of the noble metal wire be small. In view of the operation adaptability and the like, it is preferred that the diameter of the noble metal wire be 20 to 500 μm, especially 50 to 300 μm. Moreover, to ensure measurement safety, it is indispensable that the noble metal wire should not be broken by flexion or bending at the time of measurement. Namely, where a metal wire has a diameter of 100 μm, it is preferred that the Vickers microhardness be not larger than 150. To strengthen the adhesion of the insulating covering layer to the metal wire, it is preferable to use a metal wire composed of a noble metal as mentioned above, which wire is covered with a layer of a transition metal selected from those metals within the range of from atomic number 21 (scandium) to atomic number 30 (zinc). These transition metals may be used either together or in combination. Moreover, there may be adopted a multi-layer structure comprising a plurality of layers of transition metals. In view of the electrode performance, especially the stability at the initial stage of the measurement, it is preferred that the thickness of the transition metal layer be as small as possible and not larger than 10% of the diameter of the noble metal wire. If the transition metal layer has a thickness not exceeding 10% of the diameter of the noble metal wire, the transition metal layer need not be formed on the entire surface of the noble metal wire. If the transition metal layer is present to such an extent that peeling is not caused in the vicinity of the membrane, the transition metal layer need not be present in other portions. As means for forming a transition metal layer in the necessary portions, methods customarily used for forming a metal layer may be adopted. These include, for example, an electrolytic plating method, an electroless plating method, and a sputtering method.

As the material of the insulating covering layer, polymeric compounds customarily used for covering metal wires may be used, such as polyurethanes, polyesters, polyamides, and epoxy resins. As the polymeric compound having the best adhesion to the noble metal or the transition metal deposited thereon, and the highest stability to a wet heat treatment such as autoclave sterilization, there can be mentioned a crosslinked epoxy resin. For example, there may be used a resin formed by heating and curing a composition comprising a bisphenol A type epoxy resin and a phenolic resin and/or a melamine resin.

If a crosslinked epoxy resin alone is used for the insulating covering layer, cracks are liable to be formed on the epoxy resin by bending or the like and there is a possibility of pinhole formation from these cracks. Accordingly, a polyurethane which has a high resistance to cracking due to bending or other external force and has a good adhesion to a polyurethane porous membrane and a high safety to a living body is used as an outermost layer on the layer of the crosslinked epoxy resin as the inner layer. The crosslinked epoxy resin need not be covered on all the portion falling in contact with the transition metal layer, but it is sufficient if the crosslinked epoxy resin is present to such an extent that peeling is not caused in the vicinity of the porous membrane. As means for applying the crosslinked epoxy resin to the necessary portions, customary methods such as dipping, spraying, and coating can be adopted, and after application of the resin, heat curing is carried out.

To facilitate discrimination of the kind of metal electrode, it is preferred that the insulating covering layer be colored. In this case, in view of color fading caused by wet heat treatment or the like and the stability to a living body, preferably a method is adopted in which a coloring layer is formed between the inner layer of the epoxy resin and the outermost layer of the polyurethane resin.

The thickness of the insulating covering layer is determined so that electric insulating can be maintained and the electrically insulated state can be retained even if an external force, such as bending, is applied while the metal electrode is used. Namely, it is preferred that the thickness of the insulating covering layer be at least 5 μm. It is also preferred that the thickness of the crosslinked epoxy resin layer be at least 4 μm.

In the electrode for a living body according to the present invention, it is indispensable that the tip end and/or a part of the side face of the metal wire be not covered with the insulating covering layer but with a porous membrane instead. In the case of a metal electrode having the transition metal layer, it is indispensable that the tip end and/or side face of the metal electrode is covered neither with the insulating covering layer nor with the transition metal layer but with a porous membrane. This portion not covered with the insulating cover layer has a direct relationship with an effective surface area of the electrode.

As means for covering the noble metal wire with the porous membrane, a method may be adopted in which the noble metal wire having the insulating covering layer formed on the periphery thereof is cut at right angles to the longitudinal direction and the cut metal surface, or the metal surface exposed by peeling the insulating covering layer in the vicinity of the cut surface, is covered with the porous membrane.

The porous membrane used in the present invention has fine pores piercing through the membrane from the outer surface to the surface falling in contact with the metal. A porous membrane comprising an outermost dense layer having fine pores having an average pore size not larger than 0.7 μm and an inner layer contiguous to the outermost layer, which has pores having a pore size equal to or larger than the pore size of the pores of the outermost layer, is preferably used in the present invention. When the electrode covered with this porous membrane is inserted into the blood vessel or tissue, this porous membrane promptly absorbs water to form a stable water film layer surrounded by the dense outermost layer on the surface of the electrode. After passage through the pores of the outermost layer, oxygen promptly arrives at the surface of the electrode through this water film. If the average pore size of the pores in the outermost layer exceeds 0.7 μm, blood cells in the blood such as erythrocytes and platelets pass through the pores to deposit on the electrode or clog the pores, with the result that the permeation of oxygen gas is reduced. From this view point, it is preferred that the pore size of the pores in the dense layer be not larger than 0.5 μm.

The electrode sensitivity increases with an increase of the porosity of the porous membrane, but the porosity is determined by taking both the physical strength of the membrane and the electrode sensitivity into consideration. Therefore, a porous membrane having an outermost dense layer and an inner layer having a pore size equal to or larger than the pore size in the outermost dense layer is preferred.

The thickness of the porous membrane used in the present invention is determined according to the mechanical strength and the thickness necessary for forming a stable water film layer by the porous membrane, but it is ordinarily preferred that the thickness of the porous membrane be 5 to 200 μm, especially 20 to 100 μm. Of course, the thickness of the outermost dense layer should be as small as possible, within the range satisfying the requirement of the physical stability, as this ensures that diffusion of the oxygen gas is promptly effected.

Various materials have heretofore been proposed as the material for the formation of membranes having a porous structure as described above. However, these materials are defective in some points or other. For example, in the case of a hydrophobic material such as polypropylene, polytetrafluoroethylene, or silicone, if the electrode is allowed to stand in air for a long time, for example, 10 minutes, it takes a long time to obtain a stable output. Furthermore, the adhesion to the insulating covering layer is poor and the measurement stability is reduced when the measurement is conducted over a long period.

In the case of a hydrophilic material such as cellulose, polyhydroxyethyl acrylate, or cellulose acetate, as proposed by us in Japanese Unexamined Patent Publication No. 58-73342, the strength of the membrane is insufficient, the adhesion of the membrane to the insulating covering layer is insufficient, and the measurement stability is relatively poor.

We made researches with a view to developing a porous membrane material, in which a porous structure as described above can be easily formed, the membrane strength is sufficient, the measurement stability is good even if the measurement is conducted for a long time, a good resistance to sterilization, for example, autoclave sterilization or ethylene oxide sterilization, is attained, the compatibility with a living body is good and the adhesion to a polyurethane constituting the outermost layer of the insulating covering layer of the metal electrode is good. As the result, it was found that a polyurethane is most preferred as the material of the porous membrane.

The polyurethane membrane of the present invention has a porous structure as described above. Both the polyester type urethane and the polyether type urethane can be used in the present invention. In view of the stability at the long-time measurement, it is preferred that when the polyurethane is formed into a uniform and homogeneous film, the 100% modulus of the film be at least 10 kg/cm$^2$, especially at least 20 kg/cm$^2$. If this 100% modulus is lower than 10 kg/cm$^2$, the formed polyurethane porous membrane has poor pore size-retaining property and while the electrode is used, the porous structure is readily changed by an external force, for example, the contraction force of the muscle generated when the electrode is inserted into the muscle. This change of the porous structure of the membrane results in a change in the diffusion of oxygen in the membrane, and stable measurement often becomes impossible.

The polyurethane porous membrane of the present invention can be prepared, for example, according to a method comprising applying a solution of a polyurethane in an appropriate solvent to the entire metal-exposed surface of the metal electrode and removing the solvent in air, or a in a non-solvent compatible with the solvent, to effect coagulation.

When this method is adopted for formation of the porous membrane, the pore size can be adjusted by varying the composition of the solvent, the polyurethane concentration, the coagulating solution composition, or the coagulating solution temperature, or by adding a salt such as calcium chloride or sodium chloride, a non-solvent such as water or alcohol, or a surface active agent such as polyethylene glycol, to the polyurethane solution. Note, the pore size adjusting means is not limited to those mentioned above. The obtained porous membrane may be subjected to a heat treatment according to need, whereby the porous structure can be stabilized.

The porous membrane directly covers the exposed surface of the metal wire, as pointed out hereinbefore. To improve the adhesion of the thus obtained polyurethane porous membrane to the metal wire, it is preferred that not only the exposed surface of the metal wire but also the neighbouring insulating covering layer be covered with the polyurethane porous membrane. By the neighbouring insulating covering layer is meant a portion of the insulating covering layer located within a length of at least 0.5 mm from the surface of the metal wire.

The electrode for a living body, prepared according to the above-mentioned method, should be sterilized before it is actually used. This is because, during the sterilization or during the storage after the sterilization to the point of the measurement, air may have intruded into some of the pores of the polyurethane porous membrane of the electrode or the porous membrane has dried, with the result that a long time is required to obtain a stable output and the reliability of output values is reduced.

To prevent the intrusion of air or drying of the porous membrane, a method may be adopted in which the porous membrane is kept in the wet state. For example, there can be mentioned a method in which the electrode for a living body is charged in a vessel filled with water and the vessel is sealed after sterilization. When this method is adopted, if the electrode is promptly used after removal from the water-filled vessel, the characteristics of the electrode are not degraded and the measurement can be performed satisfactorily. However, if the electrode is exposed to air for a long time after removal from the water-filled vessel, a long time may be required to obtain a stable output or the reliability of output values may be reduced.

As means for preventing drying of a porous membrane, there is known a method in which hollow fibers of the porous membrane are treated with glycerol. When this method is adopted, adhered glycerol is inevitably removed by washing before the use. If this washing is not effected, glycerol is left in the porous membrane and various problems will arise. In the case of an electrode for a living body, such as the electrode of the present invention, washing is not ordinarily carried out before the measurement, and if the treatment with a compound such as glycerol is performed, it is difficult to remove the compound. Accordingly, it has been considered that this treatment would be deterious to the stability and reproducibility of the electrode. In contrast, we have found that in an electrode for a living body, such as the electrode of the present invention, a compound such as mentioned above is promptly removed so that problems do not occur, or the compound promptly absorbs and retains water to such an extent that the porous membrane is substantially filled with water and thus no problems arise during the measurement.

More specifically, according to the present invention, the above-mentioned disadvantage can be eliminated by covering at least the outer side of the polyurethane porous membrane with a compound which is easily soluble in water, has a boiling point of at least 100° C., has a very low vapor pressure at room temperature, does not cause a substantial weight decrease when allowed to stand in the open state at room temperature, and is safe to a living body. For example, glycerol, polyethylene glycol, and propylene glycol can be mentioned. Of these compounds, glycerol is most preferred from the viewpoint of the reproducibility of the outputs. If the porous membrane covered with polyethylene glycol is allowed to stand for a long time, the polyurethane membrane may become swollen and the reproducibility of the output values obtained before and after the storage reduced. Even in this case, however, the metal electrode may be used conveniently when changes in the output values are continuously measured. Moreover, even where a high precision of the absolute value is required, if the measurement is first conducted on a solution having a known concentration and calibration is then effected before the measurement, the measurement can be performed very precisely.

As means for covering the porous membrane with a compound as described above, there can be mentioned a method in which the porous membrane is filled with water or an electrolyte and the porous membrane is then dipped in the compound or an aqueous solution thereof. When the electrode covered with the above compound is used for a living body, especially a human body, the electrode should be subjected to a sterilization treatment. As the sterilization method, there can be mentioned ethylene oxide gas sterilization and γ-ray sterilization.

The shape of the electrode of the present invention may be that disclosed in U.S. Pat. No. 4,442,841. For example, the tip end of the metal wire is formed as the electrode surface and this electrode surface and the vicinity thereof are covered with the porous membrane. Furthermore, the side face of the metal wire is formed as the electrode surface and this electrode surface and the vicinity thereof are covered with the porous membrane. Still further, the tip end and contiguous side face of the metal wire are formed as the electrode surface, and this electrode surface and the vicinity thereof are covered with the porous membrane.

The electrode of the present invention will now be described with reference to the accompanying drawing. FIG. 1 is an enlarged sectional view of the tip end portion of the electrode wherein reference numeral 1 represents a porous membrane, reference numeral 2 represents an insulating covering layer, reference numeral 3 represents a noble metal wire, reference numeral 4 represents a crosslinked epoxy resin layer, and reference numeral 5 represents a transition metal layer.

The electrode for a living body according to the present invention has an excellent adhesion of the porous membrane and has a high measurement precision and a quick response characteristic, and is stable even if the measurement is conducted for a long period. Moreover, the electrode according to the present invention is advantageous in that the reproducibility of the outputs is excellent and the measurement characteristics are changed only to the least extent with the lapse of time and upon sterilization.

The present invention will now be described in detail with reference to the following examples, that by no means limit the scope of the invention.

EXAMPLE 1

A platinum wire having a diameter of 100 μm was plated with nickel to a thickness of about 0.05 μm by electrolytic plating. Then, an epoxy-phenolic resin (Inner Face Varnish B supplied by Dainippon Ink and Chemicals, Inc.) was coated on the outer side of the nickel plating layer and the heat treatment was conducted at 330° C. This operation was repeated to form a layer having a thickness of 10 μm. Then, a polyurethane resin (polyester type polyurethane supplied by Totoku Paint K.K.) was coated and heat-treated at 300° C., and this operation was repeated to form a layer having a thickness of 5 μm. Thus, an insulating covering layer having a thickness of 15 μm was formed.

This metal wire was cut into a length of 30 cm with a sharp blade at a right angle to the longitudinal direction to expose a fresh platinum section.

A polyester type polyurethane (Nippolan 5109 supplied by Nippon Polyurethane K.K.; 100% modulus of its film is 200 kg/cm$^2$) was dissolved in dimethylformamide to form a homogeneous solution having a solid concentration of 20%. The metal wire was immersed in this polyurethane solution along a length of 5 mm from the exposed platinum section and then immersed in deionized water maintained at room temperature to remove the solvent. Then, only the polyurethane-applied tip end portion of the metal wire was placed in contact with the above polyurethane solution to apply the polyurethane solution to the tip end portion. This metal was then immersed in deionized water maintained at room temperature to remove the solvent completely.

When the surface and section of the polyurethane porous membrane of the electrode and the section of the metal wire were examined by a scanning type electron microscope and an X-ray micro-analyzer, it was found that pores having an average pore size of 0.3 μm were uniformly distributed in the outermost layer of the porous membrane, and the pore size was gradually increased toward the inner layer. The thickness of the porous membrane was 25 μm. It was confirmed that good adhesion was maintained between the porous membrane and the insulating covering layer, the nickel layer was interposed between the porous membrane and platinum, and no peeling was caused.

The insulating covering layer was removed along a length of about 2 cm at the end portion opposite to the end portion covered with the polyurethane porous membrane of the thus-obtained electrode, and this electrode and the silver/silver chloride electrode as the reference electrode were connected to an oxygen partial pressure measuring apparatus.

A physiological saline solution was circulated at 37° C. at a rate of 100 ml/min by using a circulating device having gas exchange and heating portions. The tip ends of both electrodes were inserted into this circulating system. Air was then introduced into the gas exchange portion. After the physiological saline solution was saturated with air, the measurement was initiated. The measured current value was not influenced by the flow of the physiological saline solution but was constant. The current value obtained in the case of the air-saturated physiological saline solution was read as an oxygen partial pressure of 150 mmHg. When nitrogen gas was introduced into the gas exchange portion instead of air, the current value was linearly reduced from the level corresponding to 150 mmHg and arrived at a constant level corresponding to an oxygen partial pressure of 0 mmHg. The calibration curve was determined by reading this value as 0 mmHg. The oxygen gas/nitrogen gas ratio was appropriately set and the current values were measured at various oxygen gas/nitrogen gas ratios. It was found that these values conformed substantially to the above calibration curve. Thus, it was confirmed that the oxygen partial pressure could be measured with a high precision.

The electrode was then taken out from the physiological saline solution and immersed in a concentrated glycerol solution according to the Japanese Pharmacopoeia (glycerol concentration of 98%), and maintained at 60° C. for 60 minutes while the glycerol solution was sufficiently stirred. Then the electrode was removed from the glycerol solution, placed in a bag, sterilized with ethylene oxide gas, and stored at room temperature for about one month. By using the same measurement solution and oxygen partial pressure measuring apparatus as described above, the measurement was carried out in the same manner as described above. It was found that the obtained values were in conformity with the values obtained at the measurement conducted before immersion in the glycerol solution with deviations within the range of ±5% and the obtained values conformed substantially to the above-mentioned calibration curve. The time required for stabilization was as short as about 10 minutes.

Furthermore, when the measurement was continuously conducted for 100 hours in a physiological saline solution, stable current values were obtained.

After the measurement, the electrode was held between finger nails and bent around ten times. No cracks formed on the insulating covering layer.

EXAMPLE 2

Copper was deposited in a thickness of about 0.1 μm on the periphery of a platinum wire having a diameter of 150 μm, by electrolytic plating. Then, an epoxy-phenolic resin (supplied by Dainippon Ink and Chemicals, Inc.) was coated on the outer side of the copper layer and heated at 330° C. This operation was repeated to form a layer having a thickness of 10 μm. Then, a polyurethane resin (polyester type polyurethane supplied by Totoku Paint K.K.) was coated and heated at 300° C., and this operation was repeated to form a layer having a thickness of 6 μm. Thus, an insulating covering layer having a total thickness of 16 μm was formed. The metal wire was cut into a length of 20 cm at a right angle to the longitudinal direction, with a sharp blade, to expose a fresh platinum surface. The platinum wire was immersed in the same dimethylformamide solution of the polyester type polyurethane as used in Example 1 along a length of about 5 mm from the exposed platinum section and then immersed in deionized water maintained at room temperature to remove the solvent. Then, only the polyurethane-applied tip end portion of the metal wire was placed in contact with the above polyurethane solution to apply the polyurethane solution to the tip end portion. The metal wire was then immersed in deionized water maintained at room temperature to remove the solvent completely.

When this porous polyurethane membrane-covered electrode was examined by a scanning electron microscope and an X-ray microanalyzer, it was found that pores having an average pore size of about 0.5 μm were uniformly dispersed in the outermost layer of the porous membrane and the pore size was gradually increased toward the inner layer, and the pores were continuous from the outer surface of the membrane to the surface falling in contact with the platinum metal surface. It also was found that a good adhesion was maintained between the porous membrane and the insulating covering layer and the insulating covering layer was tightly bonded to platinum through the copper layer.

The insulating covering layer was removed along a length of about 2 cm in the end portion opposite to the end portion covered with the polyurethane porous membrane of the thus-obtained electrode, and by using this electrode as a working electrode, the oxygen partial pressure was measured in the same manner as described in Example 1. The time required for initial stabilization was as short as about 15 minutes and the response to the variation of the oxygen partial pressure in the solution was very good and quick. The measurement was performed stably when the measurement was continuously conducted for 80 hours.

After the measurement, the electrode was removed from the physiological saline solution and stored at room temperature for 12 hours. When the measurement was conducted again, the obtained results were the same as those obtained at the preceding measurement except that the time required for stabilization was about 30 minutes. It was confirmed that the measurement could be carried out at a high precision.

After the measurement, the electrode was immersed in deionized water and stored at room temperature for one month, and the measurement was conducted again. The time required for stabilization was again shortened to about 15 minutes, the measurement results conformed substantially to the results obtained by the first measurement, and the measurement could be performed at a high precision.

EXAMPLE 3

Nickel was deposited in a thickness of about 0.5 μm on the periphery of a platinum wire having a diameter of 100 μm, by electrolytic plating. An epoxy-phenolic-melamine resin (supplied by Dainippon Ink and Chemicals, Inc.; 100% modulus of its film is 40 kg/cm$^2$) was coated on the outer side of the nickel plating layer and heated at 350° C. This operation was repeated to form a layer having a thickness of 10 μm. Then, a polyurethane resin (supplied by Totoku Paint K.K.) was coated and heated at 300° C., and this operation was repeated to form a layer having a thickness of 6 μm. Thus, an insulating covering layer having a total thickness of 16 μm was formed. The metal wire was cut in a length of 20 cm, with a sharp blade, at a right angle to the longitudinal direction to expose a fresh platinum section.

A polyether type polyurethane (Crysbon 1846 supplied by Dainippon Ink and Chemicals, Inc.) was dissolved in dimethylformamide to form a homogeneous solution having a solid concentration of 20%. The metal wire was immersed in the polyether type polyurethane solution along a length of about 5 mm from the exposed platinum section and then immersed in deionized water maintained at room temperature to remove the solvent. Then, only the polyurethane-applied tip end portion of the metal wire was contacted with the above polyether type polyurethane solution to apply the polyurethane solution to the tip end portion. This metal wire was then immersed in deionized water maintained at room temperature to removed the solvent completely.

When the polyurethane porous membrane-covered electrode was examined by a scanning type electron microscope and an X-ray micro-analyzer, it was found that pores having an average pore size of about 0.5 μm were uniformly dispersed in the outermost layer of the porous membrane and the pore size was gradually increased toward the inner layer. It also was found that a good adhesion was maintained between the porous membrane and the insulating covering layer, and the insulating covering layer was tightly bonded to the platinum through the nickel layer.

By using the thus-obtained electrode, the oxygen partial pressure was measured in the same manner as described in Example 1. The time required for stabilization was as short as about 10 minutes, the current value promptly changed in response to changes in the oxygen partial pressure, and the oxygen partial pressure could be measured at a high precision.

After the measurement, the electrode was immersed in deionized water, subjected to autoclave sterilization, and stored at room temperature for one month.

After the storage, the electrode was removed from deionized water, and the measurement was carried out in the same manner as described above. The obtained results conformed substantially to the results obtained at the precedent measurement.

The physiological saline solution was then saturated with air, and the measurement was continuously conducted for 100 hours. The current value was stable.

EXAMPLE 4

Chromium was deposited in a thickness of 0.05 μm on the periphery of a platinum wire having a diameter of 100 μm. Then, in the same manner as described in Example 3, a layer of epoxy-phenolic-melamine resin having a thickness of 10 μm and a layer of polyurethane having a thickness of 5 μm were formed, whereby an insulating covering layer having a total thickness of 15 μm was formed. Then, in the same manner as described in Example 1, the section of the metal wire was covered with the polyester- type polyurethane porous membrane.

A good adhesion was maintained among the polyurethane porous membrane, insulating covering layer, and platinum.

By using the thus-obtained electrode, the oxygen partial pressure in a physiological saline solution equilibrated with air and maintained at 37° C. was measured in the same manner as described in Example 1 to obtain current values. The electrode was then immersed for 30 minutes in a solution of polyethylene glycol having an average molecular weight of 400, according to the Japanese Pharmacopoeia, at room temperature, and the electrode was allowed to stand at room temperature for two weeks. Current values were then obtained in the same manner as described above. The obtained values conformed with the current values obtained at the preceding measurement with deviations within the range of ±10%, and were generally larger than the values obtained at the preceding measurement. When oxygen gas was blown into the solution, the current value was simultaneously increased. When oxygen gas and nitrogen gas were blown into the solution at various ratios, the obtained current values were in proportion to the value obtained when the solution was equilibrated with air. It was confirmed that the measurement could be performed at a high precision.

Furthermore, when the measurement was continuously conducted for 80 hours, stable values were obtained.

EXAMPLE 5

Nickel was deposited in a thickness of 0.3 μm on the periphery of a gold wire having a diameter of 200 μm by electrolytic plating. Then, in the same manner as described in Example 1, a layer of the epoxy-phenolic resin having a thickness of 12 μm was formed on the outer side of the nickel layer and a layer of the polyurethane having a thickness of 7 μm was formed thereon, whereby an insulating covering layer having a total thickness of 19 μm was formed.

The metal wire was cut in a length of 30 cm, with a sharp blade, at a right angle to the longitudinal direction to expose a fresh gold section. The metal wire was immersed in the same dimethylformamide solution of the polyester type polyurethane as used in Example 1 along a length of 5 mm from the exposed section. The metal wire was then immersed in deionized water maintained at room temperature to remove the solvent. Then, only the polyurethane-applied tip end portion of the metal wire was placed in contact with the above polyurethane solution to apply the polyurethane solution to the tip end portion, and this metal wire was immersed in deionized water maintained at room temperature to remove the solvent completely.

The membrane surface and section of the obtained polyurethane porous membrane-covered electrode were examined by a scanning electron microscope and an X-ray micro-analyzer. It was found that pores having an average pore size of 0.5 μm were uniformly dispersed in the outermost layer of the porous membrane, the pore size was gradually increased toward the inner layer, and the thickness of the porous membrane was about 50 μm. It also was found that a good adhesion was maintained between the porous membrane and the insulating covering layer, the nickel layer was interposed between the insulating covering layer and the gold, and peeling was not caused.

By using the thus-obtained electrode, the oxygen partial pressure in physiological saline solution equilibriated with air and maintained at 37° C. was measured in the same manner as described in Example 1, and current values were obtained.

The electrode was then immersed for 60 minutes in a propylene glycol solution according to the Japanese Pharmacopoeia, which was maintained at 60° C. under agitation. After the temperature of the propylene glycol was lowered to room temperature, the electrode was removed from the propylene glycol solution and stored at room temperature for 2 weeks. Then, the oxygen partial pressure was measured in the same manner as described above. The obtained results conformed to the results obtained at the preceding measurement with deviations within the range of ±10%.

When the electrode was continuously used for the measurement for 80 hours, the output values were very stable.

EXAMPLE 6

An epoxy-phenolic resin (Inner Surface Varnish B supplied by Dainippon Ink and Chemicals, Inc.) was coated on the periphery of a platinum wire having a diameter of 100 μm and heated at 330° C. This operation was repeated to form a layer having a thickness of 10 μm. Then, a polyurethane resin (polyester type polyurethane supplied by Totoku Paint K.K.) was coated on the epoxy-phenolic resin layer and heated at 300° C., and this operation was repeated to form a layer having a thickness of 5 μm. Thus, an insulating covering layer having a total thickness of 15 μm was formed. The metal wire was cut in a length of 30 cm, with a sharp blade, at a right angle to the longitudinal direction to expose a fresh platinum section. The metal wire was immersed along a length of about 5 mm from the exposed fresh section in a 20% dimethylformamide solution of Nippolan 5109 used in Example 1. The metal wire was then immersed in deionized water maintained at room temperature to remove the solvent. Then, only the polyurethane-applied tip end portion of the metal wire was placed in contact with the above-mentioned polyurethane solution to apply the polyurethane solution to the tip end portion. This metal wire was then immersed in deionized water maintained at room temperature to remove the solvent completely.

When the surface and section of the polyurethane porous membrane of the electrode were examined by a scanning electron microscope, it was found that a porous membrane was formed in which pores having an average size of 0.3 μm were uniformly dispersed rn the outermost layer and the pore size was gradually increased, and the thickness of the porous membrane was about 20 μm. It was confirmed that a good adhesion was maintained between the insulating covering layer and the polyurethane porous layer.

By using the thus-obtained electrode, the oxygen partial pressure in physiological saline solution equilibriated with air and maintained at 37° C. was measured in the same manner as described in Example 1, and current values were obtained. The time required for stabilization was about 20 minutes.

After the measurement, the electrode was immersed in deionized water and stored at room temperature for one month. Then, the oxygen partial pressure was measured as described above. The time required for stabilization was about 20 minutes. The obtained current values conformed substantially to those obtained at the preceding measurement. When the measurement was continuously conducted for 60 hours in a physiological saline solution equilibrated with air, stable output values were obtained. After 60 hours, the current value gradually increased.

COMPARATIVE EXAMPLE 1

A polyurethane (polyester type polyurethane supplied by Totoku Paint K.K.) was coated on the periphery of a platinum wire having a diameter of 100 μm and heated at 300° C. This operation was repeated to form a layer having a thickness of 13 μm. The metal wire was cut in a length of 20 cm, with a sharp blade, at a right angle to the longitudinal direction to expose a fresh platinum section. The metal wire was immersed along a length of about 5 mm from the exposed fresh section in the same polyurethane solution as used in Example 1. The metal wire was then immersed in deionized water maintained at room temperature to remove the solvent. Then, only the polyurethane-applied tip end portion of the metal wire was placed in contact with the above polyurethane solution to apply the polyurethane solution to this metal wire. The tip end portion was then immersed in deionized water maintained at room temperature to remove the solvent completely. It was confirmed that a good adhesion was maintained between the polyurethane porous membrane and the insulating covering layer.

By using the thus-obtained electrode, the oxygen partial pressure of a physiological saline solution equilibriated with air and maintained at 37° C. was measured in the same manner as described in Example 1, and current values were obtained. The time required for stabilization was about 30 minutes. After the measurement, the electrode was immersed in deionized water and stored at room temperature for one month. Then, the oxygen partial pressure was measured in the same manner as described above, and current values were obtained. The time required for stabilization was about 40 minutes. The obtained values conformed substantially to those obtained at the preceding measurement. The measurement was then continuously conducted in a physiological saline solution equilibriated with air and maintained at 37° C. After 40 hours the current value began to increase gradually, although stable measurement had been possible before this point.

COMPARATIVE EXAMPLE 2

Nickel was deposited in a thickness of about 0.5 μm on the periphery of a platinum wire having a diameter of 100 μm by electrolytic plating. Then, a polyurethane resin (supplied by Totoku Paint K.K.) was coated on the outer side of the nickel layer and heated at 300° C. This operation was repeated to form a layer having a thickness of 15 μm.

The metal wire was cut in a length of 20 cm, with a sharp blade, at a right angle to the longitudinal direction to expose a fresh platinum section.

In the same manner as described in Example 1, the tip end portion of the metal wire was covered with the polyurethane porous membrane.

By using the thus-obtained electrode, the oxygen partial pressure in a physiological saline solution equilibriated with air and maintained at 37° C. was measured by the same measuring-apparatus as used in Example 1, and output values were obtained. After the measurement, the electrode was immersed in deionized water and stored at room temperature for one month. The measurement was then carried out by using this electrode in the same manner as described above. The current values conformed substantially to those obtained at the preceding measurement, the time required for stabilization was short, and high-precision measurement was possible. The electrode was then immersed in deionized water, subjected to autoclave sterilization, and stored at room temperature for one week. Then, by using this electrode, the measurement was conducted again in a physiological saline solution equilibriated with air and maintained at 37° C. The time required for stabilization was a little longer than that in the preceding measurement, and some deviations of the current values were caused.

COMPARATIVE EXAMPLE 3

Nickel was plated in a thickness of 0.5 μm on the periphery of a platinum wire having a diameter of 100 μm by electrolytic plating. Then, an epoxy-phenolic resin (Inner Surface Varnish B supplied by Dainippon Ink and Chemicals Inc.) was coated on the outer side of the nickel layer and heated at 330° C. This operation was repeated to form a layer having a thickness of 12 μm.

The metal wire was cut in a length of 20 cm, with a sharp blade, at a right angle to the longitudinal direction to expose a fresh platinum section. This exposed fresh platinum section was covered with the polyurethane porous membrane in the same manner as described in Example 1.

By using the thus-obtained electrode, the oxygen partial pressure in physiological saline solution equilibriated with air in the same apparatus in the same manner as described in Example 1, and current values were obtained. The time required for stabilization was about 10 minutes. After the measurement, the electrode was immersed in deionized water, subjected to autoclave sterilization, and stored at room temperature for one month. Then, the oxygen partial pressure was measured in the same manner as described above. The time required for stabilization was about 10 minutes. The current values conformed to those obtained at the preceding measurement with deviations within the range of ±10%. A good adhesion was maintained between the insulating covering layer and the polyurethane porous membrane. When the electrode was held between finger nails and it was bent around ten times, the insulating covering layer was cracked at the bending point.

We claim:

1. A metal electrode for a living body, which comprises a noble metal wire and an insulating covering layer formed around the periphery of the noble metal wire, wherein at least a part of the portion of the insulating covering layer falling in contact with the noble metal wire is composed of a crosslinked epoxy resin, the outermost layer of hte insulating covering layer is composed of a polyurethane, either or both of the tip end and a part of the side face of the noble metal wire is directly covered with a polyurethane porous membrane instead of the insulating covering layer, and said noble metal wire has a layer of a transition metal formed around the periphery of the noble metal wire except where the noble metal wire is directly covered with the polyurethane porous membrane.

2. A metal electrode for a living body according to claim 1, wherein the polyurethane porous membrane comprises a dense film having an average pore size not larger than 0.7 $\mu$m as the outermost layer and an inner layer contiguous to said dense film, said inner layer having a pore size equal to or larger than the pore size of the pores of the outermost layer.

3. A metal electrode for a living body according to claim 1, wherein the polyurethane constituting the polyurethane porous membrane has a 100% modulus of at least 10 kg/cm$^2$ as calculated as a uniform film of said polyurethane.

4. A metal electrode for a living body according to claim 1, wherein at least the outer side of the polyurethane porous membrane is covered with a compound selected from the group consisting of glycerol, propylene glycol and polyethylene glycol.

* * * * *